(12) United States Patent
Farmer

(10) Patent No.: US 7,374,039 B2
(45) Date of Patent: May 20, 2008

(54) METHODS AND APPARATUS FOR PROMOTING HYGIENE

(76) Inventor: Robert Theodore Farmer, 3611 Willoughby Cir., Belleville, IL (US) 62221

( * ) Notice: Subject to any disclaimer, the term of this patent is extended or adjusted under 35 U.S.C. 154(b) by 337 days.

(21) Appl. No.: 10/863,818

(22) Filed: Jun. 8, 2004

(65) Prior Publication Data

US 2005/0269217 A1    Dec. 8, 2005

(51) Int. Cl.
*B65D 69/00* (2006.01)
*B08B 3/00* (2006.01)

(52) U.S. Cl. ............... 206/229; 206/812; 134/26
(58) Field of Classification Search .......... 206/812, 206/494, 205, 568, 570, 581, 229, 277, 438, 206/363, 484, 484.2, 524.2; 428/188, 320.2, 428/321.1, 34.1; 424/443; 118/264; 383/38, 383/40, 207, 208; 134/26; 15/208, 209.1
See application file for complete search history.

(56) References Cited

U.S. PATENT DOCUMENTS

| | | | |
|---|---|---|---|
| 3,060,486 A * | 10/1962 | Lewis ................. | 401/132 |
| 3,636,922 A * | 1/1972 | Ketner ................ | 118/264 |
| 4,457,643 A | 7/1984 | Caniglia | |
| 4,563,103 A * | 1/1986 | Van Overloop et al. .... | 401/134 |
| 4,946,033 A * | 8/1990 | Conner ................ | 206/223 |
| 5,111,934 A * | 5/1992 | Morin ................. | 206/229 |
| 5,361,936 A * | 11/1994 | Cook ................. | 221/63 |
| 5,462,378 A | 10/1995 | Webb | |
| 5,487,932 A | 1/1996 | Dunshee | |
| 5,753,246 A | 5/1998 | Peters | |
| 5,765,717 A | 6/1998 | Gottselig | |
| D413,477 S | 9/1999 | Chaney | |
| 6,016,915 A | 1/2000 | Almond | |
| 6,132,841 A | 10/2000 | Guthrie et al. | |
| 6,446,795 B1 | 9/2002 | Allen et al. | |
| 6,530,477 B1 * | 3/2003 | Martorano et al. ...... | 206/524.2 |
| 2003/0084914 A1 * | 5/2003 | Simon ................. | 132/333 |
| 2003/0153091 A1 * | 8/2003 | Willard et al. .......... | 436/174 |
| 2004/0234711 A1 * | 11/2004 | Young ................. | 428/34.1 |

* cited by examiner

*Primary Examiner*—J. Gregory Pickett

(57) ABSTRACT

A towelette assembly includes a flexible towelette and a barrier material. The towelette is pre-moistened with a first fluid, and includes a cavity, an external surface, and an opposite internal surface. The cavity is defined at least partially within the towelette by the internal surface. The barrier material is positioned at least partially within the cavity. The barrier material encapsulates a second fluid within the cavity such that the barrier material is between the towelette inner surface and the second fluid. The barrier material is substantially impervious to the first and second fluids.

30 Claims, 5 Drawing Sheets

METHODS AND APPARATUS FOR PROMOTING HYGIENE

BACKGROUND OF THE INVENTION

This invention relates generally to towelette assemblies, and more specifically to methods and apparatus for promoting hygiene.

During childhood, most children are taught that washing their hands before eating is a healthy hygiene habit. Such habits are generally reiterated through adulthood. Moreover, as the number of contagious diseases and viruses has increased, disease consciousness of people in many careers has been heightened. For example, employees involved in food preparation and/or health care, are constantly reminded to practice good hygiene to facilitate reducing the risk of exposure to germs frequently encountered in their day-to-day activities.

In addition to frequently washing their hands, to further minimize their exposure to germs, many health care providers also frequently wipe their hands with towelettes that are pre-moistened with a germicidal solution, such as an alcohol/chlorhexidine solution. Known towelettes are generally packaged either in a single-use, sealed package, or are packaged in a dispenser that includes a large number of towelettes that are pulled from an opening formed in the dispenser. Known towelettes are constructed from an absorbent material that is folded into a towelette containing fluid. More specifically, at least some known single-use towelettes are stored in a sealed envelope. To facilitate reducing the evaporation of, and/or contamination to, the fluid within the towelette, at least some known envelopes are fabricated from a material that is impervious to the fluid, such as aluminum foil, lined with a thermoplastic liner.

The use of alcohol/chlorhexidine solutions is well known in the art as a broad spectrum germicidal composition that provides rapid bactericidal action and has a persistent antimicrobial effect. Moreover, such towelettes are often used in personal care applications, including, but not limited to, wiping a baby's skin after a diaper change, cleansing the skin, removing cosmetics, and/or other medical applications. However, over time, frequent use of towelettes pre-moistened with alcohol/chlorhexidine solutions may undesirably cause the user's skin to dry out and/or chafe.

BRIEF SUMMARY OF THE INVENTION

In one aspect, a towelette assembly is provided. The towelette assembly includes a flexible towelette and a barrier material. The towelette is pre-moistened with a first fluid, and includes a cavity, an external surface, and an opposite internal surface. The cavity is defined at least partially within the towelette by the internal surface. The barrier material is positioned at least partially within the cavity and encapsulates a second fluid within the cavity such that the barrier material extends between the towelette inner surface and the second fluid. The barrier material is substantially impervious to the first and second fluids.

In another aspect, a packaged towelette assembly is provided. The towelette assembly includes a towelette, a barrier material, and a sealed envelope. The towelette includes a disposable sheet that is suitable in size and strength for a single use wiping of the hands of a user. The towelette also includes an external surface, a cavity, and an internal surface, and is pre-moistened with a first fluid that is configured to provide broad-spectrum disinfecting activity to the towelette. The cavity is at least partially defined within said towelette by the internal surface. The barrier material is positioned at least partially within the towelette cavity, and encapsulates a second fluid within the cavity such that said barrier material is positioned between the towelette inner surface and the second fluid. The barrier material is substantially impervious to the first and second fluids. The envelope retains the sheet and barrier material, and is tearable to permit selective access to the towelette.

In a further aspect, a method for promoting hygiene is provided. The method comprises removing a towelette from an envelope, wherein the towelette is pre-moistened with a first fluid that provides a broad-spectrum disinfecting activity to the towelette, and wiping the hands of a user with the towelette and the first fluid. The method also comprises discharging a second fluid from a cavity defined within the towelette, wherein the second fluid is encapsulated within the cavity by a barrier material extending between the second fluid and an inner surface of the towelette such that the second fluid is not dischargeable from the towelette cavity without tearing at least a portion of at least one of the towelette and the barrier material, and wiping the hands of the user with the second fluid.

DETAILED DESCRIPTION OF THE INVENTION

Figure 1:
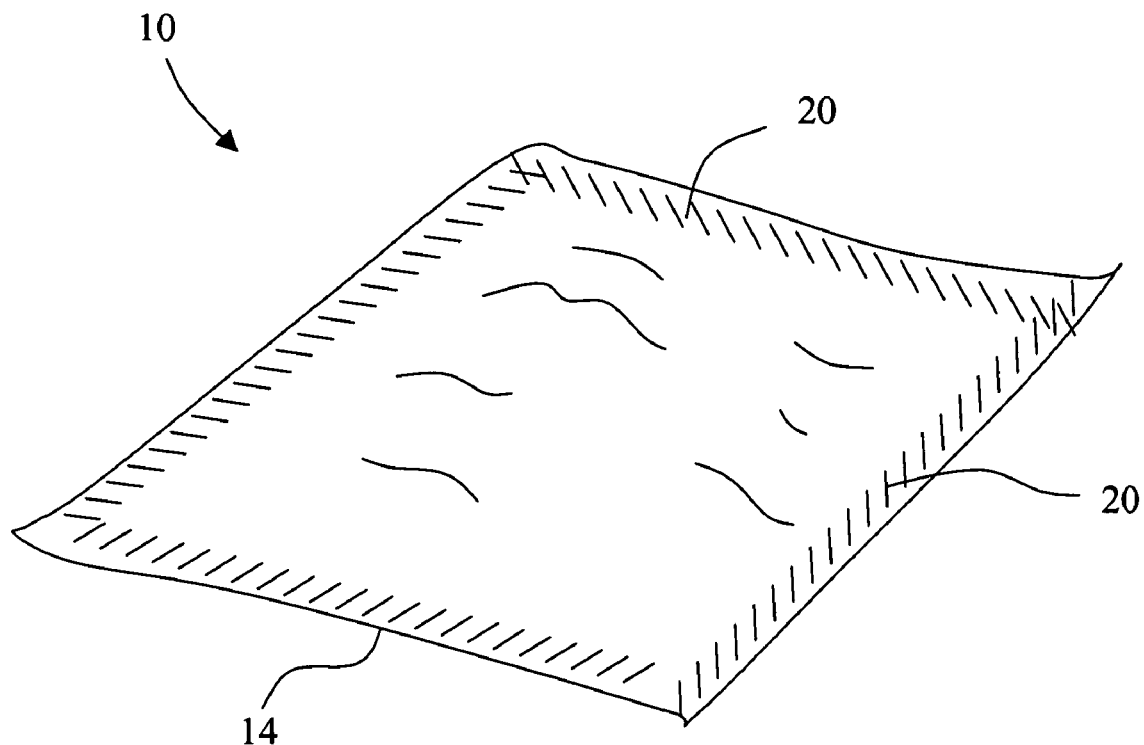
FIG. 1 is a perspective view of an exemplary towelette assembly in an unopened sealed position.
Figure 2:
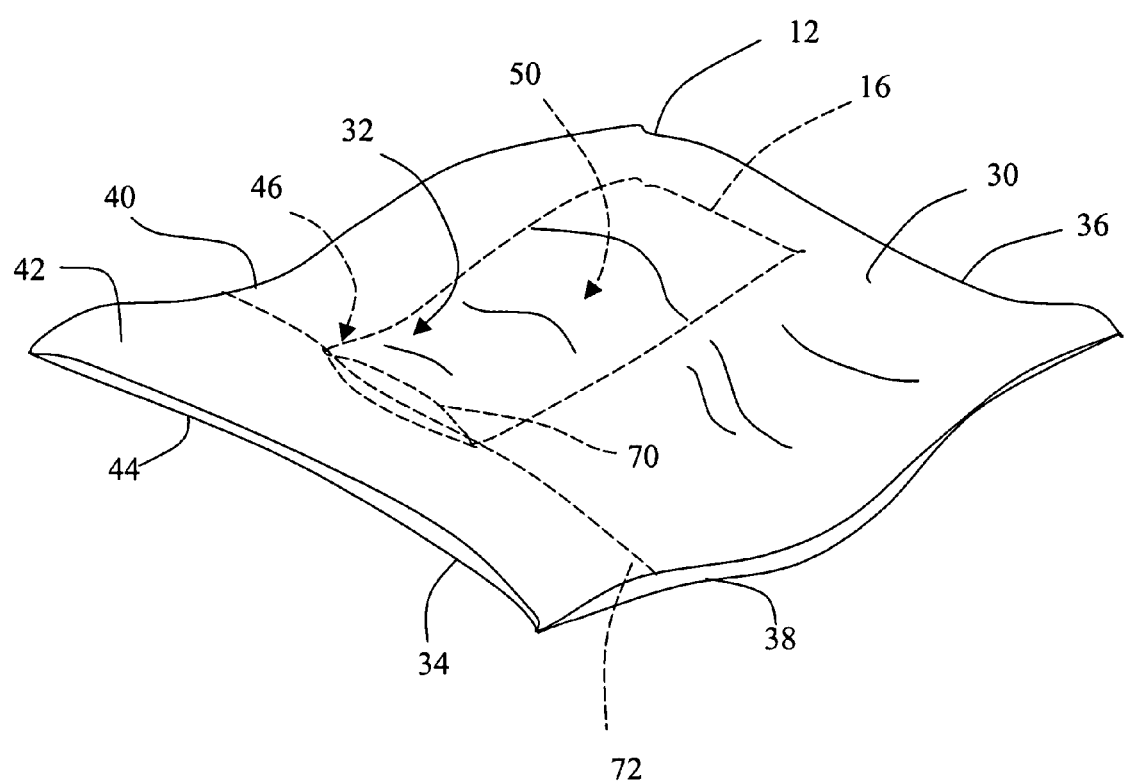
FIG. 2 is a perspective view of an exemplary towelette that may be used with the towelette assembly shown in FIG. 1.

FIG. 1 is a perspective view of an exemplary towelette assembly 10 in an unopened sealed position. FIG. 2 is a perspective view of an exemplary towelette 12 that may be used with towelette assembly 10. Towelette assembly 10 includes an envelope 14, a towelette, such as towelette 12, and a barrier film 16. In the exemplary embodiment, towelette 12 is contained within a cavity (not shown) defined within envelope 14, and is a single-use, disposable towelette. In an alternative embodiment, towelette is a multi-use towelette. Specifically, outer edges 20 of towelette 12 are bonded together in sealing contact around a perimeter of envelope 12 such that a substantially fluid-tight and air-tight bond is created around the envelope perimeter. In the exemplary embodiment, envelope 14 is rectangular-shaped and fabricated from a material that enables a user to easily tear envelope 14 by hand to access towelette 12. Alternatively, envelope 14 is non-rectangular shaped. In an alternative embodiment, envelope 14 is fabricated with a tear-line (not shown) which enables a user to easily tear envelope 14 by hand to access towelette 12.

Towelette envelopes 14 are known in the art and are hermetically-sealed and fabricated from a material which is relatively impermeable to fluids contained therein and to any vapor or gas formed therefrom. Accordingly, envelope 14 facilitates preventing fluids contained within the envelope cavity from evaporating. Moreover, the material used in fabricating envelopes 14 is also substantially impervious to air and other materials that might otherwise contaminate materials, such as the fluids or towelette 12, contained within envelope 14. In one embodiment, envelope 14 is fabricated from, but is not limited to being fabricated from, a foil-based material or a polypropylene material. In another embodiment, envelope 14 is fabricated from a combination of polypropylene material and laminates of polypropylene with other layers, such as a polypropylene/aluminum foil/polystyrene laminate, such as is commercially available from Marsh Biomedical Products, Rochester, N.Y. In a further embodiment, envelope 14 is fabricated from an aluminum foil with a thermoplastic liner, for example. In yet another embodiment, envelope 14 is fabricated from any material which enables envelope 14 to function as described herein.

In the exemplary embodiment, towelette 12 is rectangular-shaped and includes an external surface 30 and an internal surface 32. In alternative embodiments, towelette 12 is non-rectangular shaped. Each surface 30 and 32 extends lengthwise between a pair of opposed edges 34 and 36, and widthwise between a second pair of opposed edges 38 and 40.

Edges 34, 36, 38, and 40 are bonded together between opposing sides 42 and 44 of towelette 12, such that an internal cavity 46 is defined within towelette 12 by internal surface 32. In the exemplary embodiment, cavity 46 extends lengthwise and widthwise through substantially all of towelette 12 such that cavity 46 is generally bounded by edges 34, 36, 38, and 48. Alternatively, cavity 46 extends only partially through towelette 12 and as such may only be partially bounded by any, all, or none of edges 34, 36, 38, and/or 40.

In the exemplary embodiment, towelette 12 is formed as a flexible sheet of material that is multi-folded to be received within envelope 14. In an alternative embodiment, towelette 12 is packaged within a dispenser (not shown) that includes a large number of towelettes 12 that are dispensed sequentially from the dispenser through an opening (not shown) formed in the dispenser.

Towelette 12 is pre-moistened with a known fluid that provides a broad-spectrum disinfecting activity to towelette 12. More specifically, in the exemplary embodiment, when imparted to towelette 12, the towelette fluid facilitates creating an effective anti-bacterial towelette for use against commonly encountered bacteria. For example, in one embodiment, towelette 12 is pre-moistened with an alcohol solution, such as, but not limited to, an alcohol/chlorhexidine solution. Alternatively, towelette 12 may be pre-moistened with any other fluid that enables towelette 12 to function as described herein, such as, but not limited to disinfectants, cleansers, antiseptics, antibiotics, antivirals, antifungals, medications/medicaments, fragrances, cosmetics, toiletries, or any combination thereof.

Accordingly, a material used in fabricating towelette 12 is variably selected based on the fluid being impregnated into towelette 12. For example, in one embodiment, towelette 12 is fabricated from, but is not limited to being fabricated from, a cotton fabric, a felt fabric, a non-woven fabric, cellulose, a foam, or any other material, or combination of materials, including polyester resins, polyethylene terephathalate (PET), or polyester polypropylene blends, conventionally used in towelettes or wipes, and that will enable towelette 12 to function as described herein. In another embodiment, towelette 12 is fabricated from any material which enables towelette 12 to function as performed herein.

Barrier film 16 is contained within towelette cavity 46, and encapsulates a second fluid therein. Specifically, in the exemplary embodiment, towelette inner surface 32 encapsulates barrier film 16 within cavity 46. More specifically, in the exemplary embodiment, barrier film 16 is formed in a container-like shape that defines a cavity 50 therein. A fluid contained within cavity 50 is encapsulated by barrier film 16. In an alternative embodiment, barrier film 16 extends within towelette cavity 46 to facilitate preventing contact between the second fluid and towelette internal surface 32, and to contain barrier film 16 therein. For example, in one embodiment barrier film 16 is bonded against internal surface 32.

As is known in the art, the use of certain germicidal disinfectant fluids may cause a skin-drying effect to the user. In the exemplary embodiment, barrier film 16 encapsulates a moisturizing fluid that facilitates countering a skin-drying effect of the germicidal disinfectant impregnated within towelette 12. For example, in one embodiment, barrier film 16 encapsulates a moisturizing fluid including, but not limited to, a solution of aloe vera and cocoa butter. The moisturizing fluid encapsulated by barrier film 16 may be any of, and is not limited to being, a liquid, a gel, a cream, an emulsion, a solid, or any combination of the above. In an alternative embodiment, barrier film 16 encapsulates a second towelette that is impregnated with the moisturizing fluid.

Accordingly, the material used in fabricating barrier film 16 is variably selected based on the moisturizing fluid being encapsulated by barrier film 16, as well as being impervious to the towelette fluid. For example, in one embodiment, barrier film 16 is fabricated from, but is not limited to being fabricated from, a foil-based material lined with a thermoplastic material. In another embodiment, barrier film 16 is fabricated from a thermoplastic material, such as, but not limited to, a cellulose ester, mixed esters of cellulose esters, low density polyethylene (LDPE), nylons and polymeric materials, or any other material that may be formed into a film or sheet to enable barrier film 16 to function as described herein. In another alternative embodiment, barrier film 16 is fabricated from any material that enables barrier film 16 to function as described herein.

In the exemplary embodiment, barrier film 16 and towelette 12 are each fabricated with a respective tear line 70 and 72. In an alternative embodiment, at least one of barrier film 16 or towelette 12 includes a plurality of tear lines. Each tear line 70 and 72 is pre-fabricated to enable a user to easily tear a portion of barrier film 16 and/or towelette 12 by hand. More specifically, in the exemplary embodiment, towelette tear line 72 at least partially circumscribes towelette 12 and facilitates a user gaining selective access to towelette cavity 46 and barrier film 16. In one embodiment, towelette tear line 72 circumscribes a portion of towelette 12 such that when tear line 72 is ruptured, towelette 12 is divisible into at least two portions. In another embodiment, tear line 72 extends only partially across either side 42 and/or 44. In a further alternative embodiment, towelette 12 does not include tear line 72.

In the exemplary embodiment, tear line 70 at least partially circumscribes a portion of barrier film 16 and facilitates selective discharge of the moisturizing fluid from barrier film cavity 50. In one embodiment, barrier film tear line 70 circumscribes a portion of barrier film 16 such that when tear line 70 is ruptured, barrier film 16 is divisible into at least two portions. In another embodiment, tear line 70 extends only partially around barrier film 16.

In the exemplary embodiment, barrier film 16 is positioned relative to towelette 12 such that barrier film tear line 70 is substantially co-linear with respect to towelette tear line 72. Accordingly, tear lines 70 and 72 may be ruptured in the same tearing action by the user. In an alternative embodiment, barrier film 16 is positioned relative to towelette 12 such that tear lines 70 and 72 are not co-linear with respect to each other.

During use, a user initially tears envelope 14 to access towelette 12, and removes a folded towelette 12 from the envelope cavity. Towelette 12 is unfolded and wiped over the area to be cleaned or disinfected, such as the user's hands. Specifically, as towelette 12 is wiped over the area to be disinfected the fluid impregnated within towelette 12 facilitates reducing the user's exposure to commonly encountered bacteria.

After the disinfectant has been spread across the area to be disinfected, the user accesses the moisturizing fluid to moisturize the area and to facilitate preventing the skin-drying effect that may occur when using a germicidal disinfectant. Specifically, in the exemplary embodiment, as the user ruptures towelette tear line 70, barrier film tear line 72 is also ruptured to enable the moisturizing fluid to be discharged from barrier film cavity 50. Spreading the moisturizing fluid from barrier cavity 50 across the area which was wiped with the germicidal disinfectant facilitates countering potential drying effects induced by the germicidal disinfectant.

Figure 3:
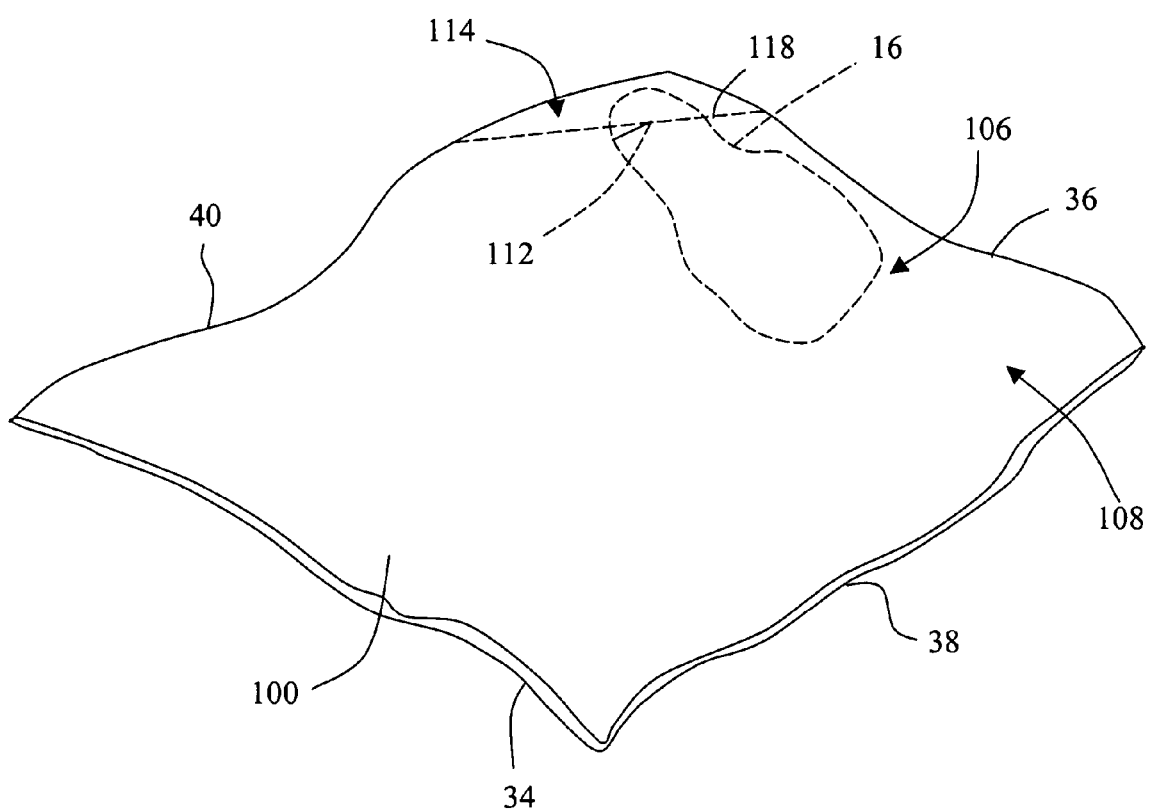
FIG. 3 is a perspective view of an alternative embodiment of a towelette that may be used with the towelette assembly shown in FIG. 1.

FIG. 3 is a perspective view of an alternative embodiment of a towelette 100 that may be used with towelette assembly 10 (shown in FIG. 1). Towelette 100 is substantially similar to towelette 12 (shown in FIG. 2) and components of towelette 100 that are identical to components of towelette 12 are identified in FIG. 3 using the same reference numerals used in FIG. 2. Accordingly, towelette 100 includes external and internal surfaces 30 and 32, and each surface 30 and 32 extends between edges 34 and 36, and between edges 38 and 40.

Edges 34, 36, 38, and 40 are bonded together between opposing sides 42 and 44 of towelette 12, such that an internal cavity 106 is defined within towelette 100 by internal surface 32. However, unlike cavity 46 (shown in FIG. 2), cavity 106 extends lengthwise through only a portion 108 of towelette 100 and widthwise across towelette 100. Accordingly, in the exemplary embodiment, towelette cavity 106 is bounded by only one edge 36, and by a portion of edge 38. In an alternative embodiment, cavity 106 only partially across towelette 100 and as such, may only be partially bounded by any of edges 34, 36, 38, and/or 40. In a further alternative embodiment, towelette cavity 106 is positioned such that cavity 106 is not bounded by any of edges 34, 36, 38, or 40, and as such is entirely defined by only inner surface 32.

Similar to towelette 12, towelette 100 is also pre-moistened with a known fluid that provides a broad-spectrum disinfecting activity to towelette 100. More specifically, in the exemplary embodiment, when imparted to towelette 100, the towelette fluid facilitates creating an effective antibacterial towelette for use against commonly encountered bacteria. Accordingly, a material used in fabricating towelette 100 is variably selected based on the fluid being impregnated into towelette 100.

Barrier film 16 is contained within towelette cavity 106, and encapsulates a second fluid therein. Specifically, in the exemplary embodiment, towelette inner surface 32 encapsulates barrier film 16 within cavity 106. In an alternative embodiment, barrier film 16 extends through towelette cavity 106 to facilitate preventing contact between the second fluid and towelette internal surface 32, and to contain barrier film 16 therein. For example, in one embodiment barrier film 16 is bonded against internal surface 32.

Barrier film 16 and towelette 100 are each fabricated with a respective tear line 110 and 112. In an alternative embodiment, at least one of barrier film 16 or towelette 100 includes a plurality of tear lines. Each tear line 110 and 112 is pre-fabricated to enable a user to easily tear a portion of barrier film 16 and/or towelette 100 by hand. More specifically, in the exemplary embodiment, towelette tear line 112 extends obliquely between a pair of towelette edges 36 and 40 to enable at least a portion 114 of towelette 100 to be removed when tear line 112 is ruptured. Moreover, rupturing tear line 112 facilitates providing a user selective access to the moisturizing fluid contained within barrier film 16.

In the exemplary embodiment, tear line 110 extends obliquely across barrier film 16 such that at least a portion 118 of barrier film 16 is removable when tear line 10 is ruptured. More specifically, in the exemplary embodiment, barrier film 16 is positioned relative to towelette 100 such that barrier film tear line 110 is substantially co-linear with respect to towelette tear line 112. Accordingly, tear lines 110 and 112 may be ruptured in the same tearing action by the user. In an alternative embodiment, barrier film 16 is positioned relative to towelette 100 such that tear lines 110 and 112 are not co-linear with respect to each other.

Figure 4:
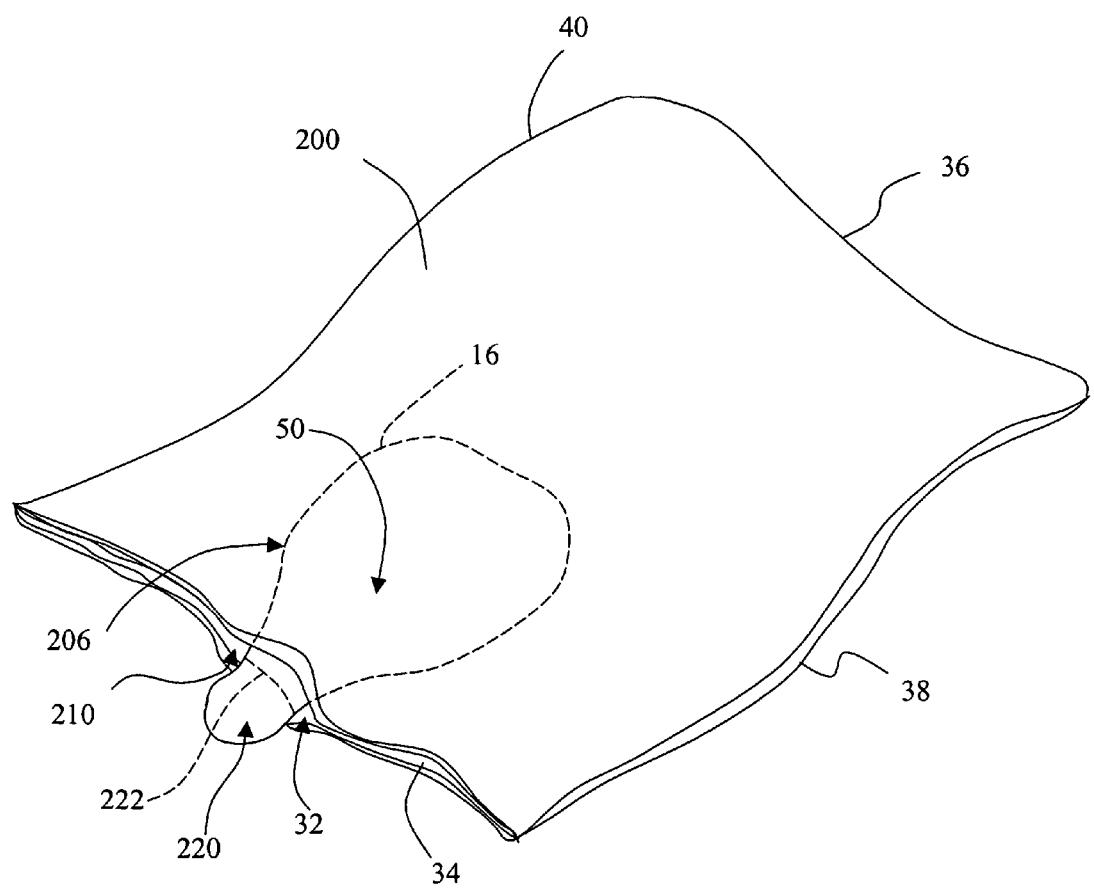
FIG. 4 is a perspective view of a further alternative embodiment of a towelette that may be used with the towelette assembly shown in FIG. 1.

FIG. 4 is a perspective view of a further alternative embodiment of a towelette 200 that may be used with towelette assembly 10 (shown in FIG. 1). Towelette 200 is substantially similar to towelettes 12 and 100 (shown in FIGS. 2 and 3) and components of towelette 200 that are identical to components of towelettes 12 and 100 are identified in FIG. 4 using the same reference numerals used in FIGS. 2 and 3. Accordingly, towelette 200 includes external and internal surfaces 30 and 32, and each surface 30 and 32 extends between edges 34 and 36, and between edges 38 and 40.

Edges 34, 36, 38, and 40 are bonded together between opposing sides 42 and 44 of towelette 12, such that an internal cavity 206 is defined within towelette 200 by internal surface 32. However, unlike cavity 46 (shown in FIG. 2) and cavity 106 (shown in FIG. 3), cavity 206 is not defined by a sealed perimeter, but rather cavity 206 includes an opening 210 that extends through an unsealed portion of at least one edge 34, 36, 38, or 40. More specifically, in the exemplary embodiment, opening 210 extends from edge 34 into cavity 206.

Barrier film 16 is at least partially contained within towelette cavity 206, and encapsulates a second fluid therein. Specifically, in the exemplary embodiment, barrier film 16 is formed in a container-like shape that defines cavity 50 therein such that a fluid contained within cavity 50 is encapsulated by barrier film 16. At least a portion 220 of barrier film 16 extends radially outward from cavity 206 and through opening 210.

Accordingly, in the exemplary embodiment, only barrier film 16 is fabricated with a tear line 222. Tear line 222 is pre-fabricated to enable a user to easily tear barrier film portion 220 by hand to facilitate providing a user selective access to the moisturizing fluid contained within barrier film cavity 50. Accordingly, when tear line 222 is ruptured, portion 220 is removable from barrier film 16.

Figure 5:
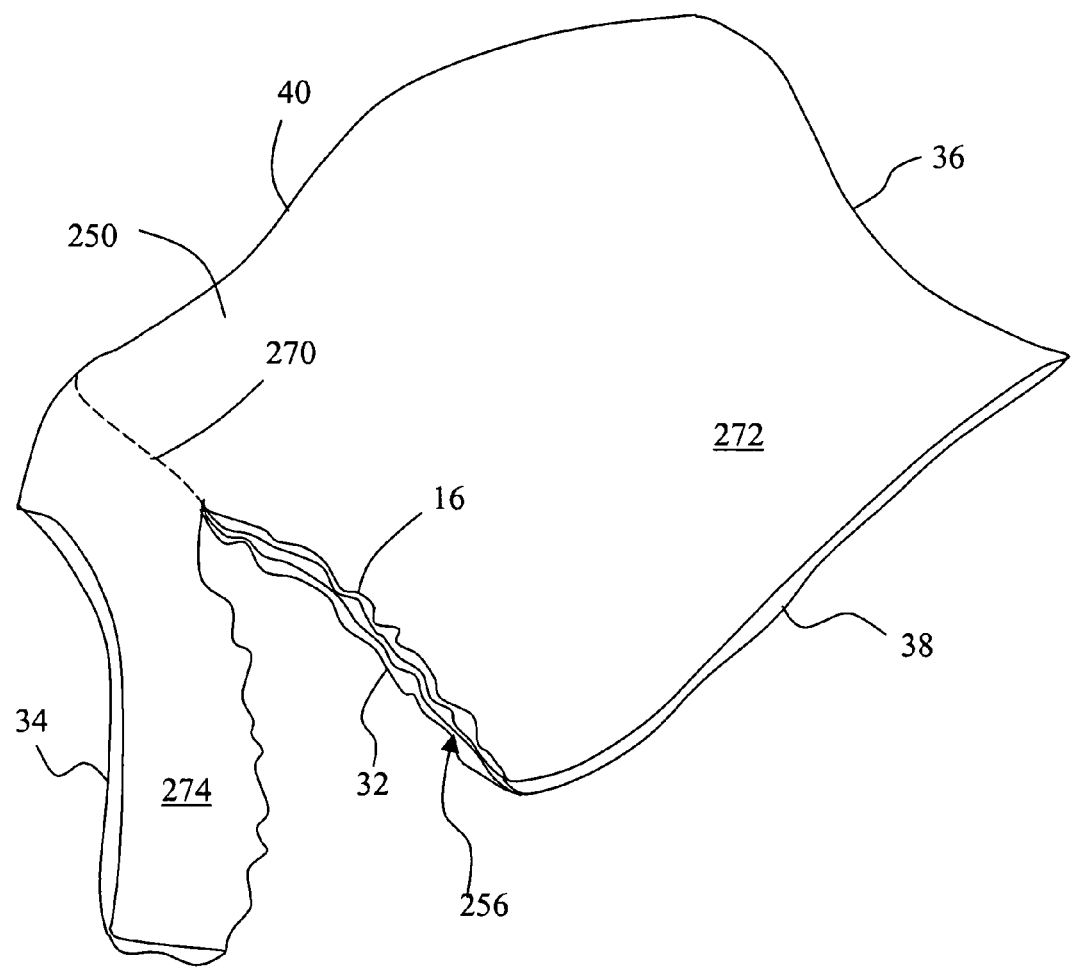
FIG. 5 is a perspective view of another alternative embodiment of a towelette that may be used with the towelette assembly shown in FIG. 1, and in a partially ruptured position.

FIG. 5 is a perspective view of another alternative embodiment of a towelette 250 that may be used with towelette assembly 10 (shown in FIG. 1), and in a partially ruptured condition. Towelette 250 is substantially similar to towelettes 12, 100, and 200 (shown in FIGS. 2-4) and components of towelette 250 that are identical to components of towelettes 12, 100, and/or 250 are identified in FIG. 5 using the same reference numerals used in FIGS. 2-4. Accordingly, towelette 250 includes external and internal surfaces 30 and 32, and each surface 30 and 32 extends between edges 34 and 36, and between edges 38 and 40.

Edges 34, 36, 38, and 40 are bonded together between opposing sides 42 and 44 of towelette 12, such that an internal cavity 256 is defined within towelette 250 by internal surface 32. In the exemplary embodiment, cavity 256 is bounded by edges 34, 36, 38, and 40. Alternatively, cavity 256 extends only partially through towelette 206 and as such, may only be partially bounded by any, all, or none of edges 34, 36, 38, and/or 40.

Barrier film 16 is contained within towelette cavity 256 and encapsulates a second fluid therein. Specifically, in the exemplary embodiment, barrier film 16 is bonded against towelette inner surface 32. For example, in one embodiment, barrier film 16 is fabricated from a thermoplastic material, such as a polypropylene material, that enables film 16 to be heat-sealed against inner surface 32. In another embodiment, barrier film 16 is fabricated from a material that enables film 16 to be bonded to inner surface 32 through an adhesive process. More specifically, the material used in fabricating barrier film 16 is variably selected based on the moisturizing fluid being encapsulated by barrier film 16, as well as being impervious to the towelette fluid and being bondable to inner surface 32. For example, in one embodiment, barrier film 16 is fabricated from, but is not limited to being fabricated from, a foil-based material lined with a thermoplastic material. In another embodiment, barrier film 16 is fabricated from a thermoplastic material, such as, but not limited to, a cellulose ester, mixed esters of cellulose esters, low density polyethylene (LDPE), nylons and polymeric materials, or any other material that may be formed into a film or sheet to enable barrier film 16 to function as described herein.

In the exemplary embodiment, towelette 250 is fabricated with a tear line 270 that is pre-fabricated to enable a user to easily tear towelette 250 by hand. More specifically, in the exemplary embodiment, towelette tear line 270 at least partially circumscribes towelette 250 and facilitates a user gaining selective access to fluid contained within barrier film 16. Moreover, in the exemplary embodiment, towelette tear line 270 circumscribes a portion of towelette 250 such that when tear line 270 is ruptured, towelette 250 is divisible into at least two portions 272 and 274.

The above-described towelette assemblies are cost-effective and highly reliable. Each assembly includes a towelette that at least partially contains a barrier material therein. The flexible towelette is pre-moistened with a germicidal disinfectant that promotes hygiene and provides a broad-spectrum disinfecting activity to the towelette. The barrier film encapsulates a moisturizing fluid therein and is substantially impervious to the first and second fluids such that contact between the moisturizing fluid and the towelette is prevented. Rupturing at least one tear line enables a user to selectively discharge the moisturizing fluid to facilitate countering a drying effect that may be induced by frequent use of the germicidal disinfectant fluid. As a result, the towelette assembly facilitates promoting hygiene and reducing the effects of exposure to germs to a user without increasing the drying effect that may be induced to the user that is commonly associated with frequent use of germicidal disinfectants.

Exemplary embodiments of towelette assemblies are described above in detail. The assemblies are not limited to the specific embodiments described herein, but rather, components of each towelette assembly may be utilized independently and separately from other components described herein. For example, each aspect of each towelette and/or barrier material may also be used in combination with other towelettes, barrier materials, and/or towelette assemblies.

While the invention has been described in terms of various specific embodiments, those skilled in the art will recognize that the invention can be practiced with modification within the spirit and scope of the claims.

What is claimed is:

1. A towelette assembly comprising:
    a flexible towelette pre-moistened with a first fluid, said towelette comprising a cavity, an external surface, and an opposite internal surface, said cavity defined at least partially within said towelette by said internal surface; and
    a barrier material positioned at least partially within said cavity, said barrier material encapsulating a second fluid within said cavity such that said barrier material is between said to the first and second fluids, at least one of said towelette and said barrier material comprises at least one tear line that facilitates selective discharge of the second fluid from said cavity without the second fluid contacting said towelette.

2. A towelette assembly in accordance with claim 1 wherein said at least one tear line creates an opening in said cavity when a shear force is applied to said at least one tear line.

3. A towelette assembly in device in accordance with claim 1 wherein said at least one tear line substantially circumscribes at least one of said towelette and said barrier material, said towelette assembly is divisible by hand into two sections by rupturing said at least one tear line along its entire length.

4. A towelette assembly in accordance with claim 1 wherein said barrier material comprises at least one of a foil-based material and a thermoplastic material.

5. A towelette assembly in accordance with claim 1 wherein said barrier material is further configured to prevent contamination and evaporation of the second fluid contained within said towelette cavity.

6. A towelette assembly in accordance with claim 1 wherein the first fluid is selected from a group consisting of a cleanser, a medicament, a moisturizer, a cosmetic, a toiletry, an antiseptic, and a disinfectant.

7. A towelette assembly in accordance with claim 1 wherein said barrier material is formed against at least a portion of said towelette inner surface.

8. A towelette assembly comprising:
    a flexible towelette pre-moistened with a first fluid, said towelette comprising a cavity, an external surface, and an opposite internal surface, said cavity defined at least partially within said towelette by said internal surface; and
    a barrier material positioned at least partially within said cavity, said barrier material encapsulating a second fluid within said cavity such that said barrier material is between said towelette inner surface and the second fluid, said barrier material is substantially impervious to the first and second fluids, at least a portion of said barrier material extends outward from said cavity.

9. A towelette assembly in accordance with claim 1 further comprising a tearable envelope, said towelette and said barrier material contained within said envelope.

10. A towelette assembly in accordance with claim 1 further comprising a container defined by said barrier material, said container positioned at least partially within said cavity.

11. A packaged towelette assembly comprising:
   a towelette comprising a disposable sheet suitable in size and strength for single use wiping of the hands of a user, said towelette comprising an external surface, a cavity, and an internal surface, said towelette pre-moistened with a first fluid configured to provide broad-spectrum disinfecting activity to said towelette, said cavity is at least partially defined within said towelette by said internal surface;
   a barrier material positioned at least partially within said towelette cavity, said barrier material encapsulating a second fluid within said cavity such that said barrier material is between said towelette inner surface and the second fluid, said barrier material is substantially impervious to the first and second fluids, at least one of said towelette and said barrier material comprises at least one tear line that facilitates selective discharge of the second fluid from said cavity without the second fluid contacting said towelette; and
   a sealed envelope retaining said sheet and said barrier material, said envelope is tearable to permit selective access to said towelette.

12. A towelette assembly in accordance with claim 11 wherein said at least one tear line circumscribes at least a portion of said barrier material, said at least one tear line facilitates selective discharge of the second fluid from said towelette cavity.

13. A towelette assembly in accordance with claim 11 wherein said at least one tear line extends at least partially between said internal and external surfaces, said at least one tear line is tearable by hand for creating at least one opening in said towelette cavity along said at least one tear line.

14. A towelette assembly in accordance with claim 11 wherein said at least one tear line extends at least partially between said internal and external surfaces, said at least one tear line is tearable by hand for creating at least one opening in said towelette cavity and said barrier material for selective discharge of the second fluid from said towelette cavity.

15. A towelette assembly in accordance with claim 11 wherein said at least one tear line extends at least partially between said internal and external surfaces, said at least one tear line is tearable by hand for creating at least one opening in said barrier material for selective discharge of the second fluid from said towelette cavity.

16. A towelette assembly in accordance with claim 11 wherein said at least one tear line substantially circumscribes a portion of at least one of said towelette and said barrier material.

17. A towelette assembly in accordance with claim 16 wherein at least one of said towelette and said barrier material is divisible by hand into two sections by tearing said at least one tear line along its entire length.

18. A towelette assembly in accordance with claim 11 wherein said barrier material comprises at least one of a foil-based material and a thermoplastic-based material.

19. A towelette assembly in accordance with claim 11 wherein said envelope is impervious to the first and second fluids.

20. A towelette assembly in accordance with claim 11 wherein said envelope facilitates preventing contamination and evaporation of the first fluid, said barrier material facilitates preventing contamination and evaporation of the second fluid.

21. A towelette assembly in accordance with claim 11 wherein said barrier material is formed against at least a portion of said towelette internal surface.

22. A towelette assembly in accordance with claim 11 wherein said towelette is pre-moistened with a fluid selected from the group consisting of a cleanser, a medicament, a cosmetic, a toiletry, an antiseptic, and a disinfectant.

23. A packaged towelette assembly comprising:
   a towelette comprising a disposable sheet suitable in size and strength for single use wiping of the hands of a user, said towelette comprising an external surface, a cavity, and an internal surface, said towelette pre-moistened with a first fluid configured to provide broad-spectrum disinfecting activity to said towelette, said cavity is at least partially defined within said towelette by said internal surface;
   a barrier material positioned at least partially within said towelette cavity, said barrier material encapsulating a second fluid within said cavity such that said barrier material is between said towelette inner surface and the second fluid, said barrier material is substantially impervious to the first and second fluids, wherein said barrier material extends at least partially from said towelette cavity; and
   a sealed envelope retaining said sheet and said barrier material, said envelope is tearable to permit selective access to said towelette.

24. A method for promoting hygiene, said method comprising:
   removing a towelette from an envelope, wherein the towelette is pre-moistened with a first fluid that provides a broad-spectrum disinfecting activity to the towelette;
   wiping the hands of a user with the towelette;
   discharging a second fluid from a cavity defined within the towelette such that the second fluid does not contact the towelette, wherein the second fluid is encapsulated within the cavity by a barrier material extending between the second fluid and an inner surface of the towelette such that the second fluid is not dischargable from the towelette cavity without tearing at least a portion of at least one of the towelette and the barrier material; and
   wiping the hands of the user with the second fluid.

25. A method in accordance with claim 24 wherein removing a towelette from an envelope further comprises tearing the envelope by hand to permit removal of the towelette from the envelope.

26. A method in accordance with claim 24 wherein discharging a second fluid from a cavity defined within the towelette further comprises rupturing a tear line that is pre-formed in at least one of the towelette and the barrier material.

27. A method in accordance with claim 26 wherein rupturing a tear line that is pre-formed in at least one of the towelette and the barrier material further comprises rupturing the pre-formed tear line by hand.

28. A method for promoting hygiene, said method comprising:
   removing a towelette from an envelope, wherein the towelette is pre-moistened with a first fluid that provides a broad-spectrum disinfecting activity to the towelette;
   wiping the hands of a user with the towelette;
   discharging a second fluid from a cavity defined within the towelette, wherein the second fluid is encapsulated within the cavity by a barrier material extending between the second fluid and an inner surface of the towelette such that the second fluid is not dischargable from the towelette cavity without tearing at least a portion of at least one of the towelette and the barrier material, and such that at least one of the towelette and the barrier material is divided into at least two portions by rupturing a tear line formed in at least one of the towelette and the barrier material; and wiping the hands of the user with the second fluid.

29. A method in accordance with claim 28 wherein dividing at least one of the towelette and the barrier material into at least two portions further comprises rupturing the tear line by hand along a full length of the tear line.

30. A method in accordance with claim 24 wherein wiping the hands of user with the towelette further comprises wiping the hands of the user with a towelette pre-moistened with a fluid selected from the group consisting of a cleaner, a medicament, a moisturizer, a cosmetic, a toiletry, an antiseptic, and a disinfectant.

* * * * *